(12) United States Patent
Hu

(10) Patent No.: US 11,379,922 B2
(45) Date of Patent: Jul. 5, 2022

(54) BLOCKCHAIN-BASED SERVICE PROCESSING

(71) Applicant: Advanced New Technologies Co., Ltd., Grand Cayman (KY)

(72) Inventor: Duofeng Hu, Hangzhou (CN)

(73) Assignee: Advanced New Technologies Co., Ltd., Grand Cayman (KY)

( * ) Notice: Subject to any disclaimer, the term of this patent is extended or adjusted under 35 U.S.C. 154(b) by 46 days.

(21) Appl. No.: 16/749,345

(22) Filed: Jan. 22, 2020

(65) Prior Publication Data

US 2020/0160452 A1 May 21, 2020

(30) Foreign Application Priority Data

Jan. 22, 2019 (CN) .......................... 201910059350.8

(51) Int. Cl.
*G06Q 40/08* (2012.01)
*G16H 10/60* (2018.01)
(Continued)

(52) U.S. Cl.
CPC ......... *G06Q 40/08* (2013.01); *G06F 16/2379* (2019.01); *G16H 10/60* (2018.01); *G16H 15/00* (2018.01)

(58) Field of Classification Search
None
See application file for complete search history.

(56) References Cited

U.S. PATENT DOCUMENTS 10,354,236 B1 7/2019 Wang
10,867,057 B1 * 12/2020 Knas .................... G06F 21/44
(Continued)

FOREIGN PATENT DOCUMENTS

CN 108197891 6/2018
CN 108629565 10/2018
(Continued)

OTHER PUBLICATIONS

Benchoufi, M., Porcher, R., & Ravaud, P. (2017). Blockchain protocols in clinical trials: Transparency and traceability of consent. F1000Research, 6. (Year: 2017).*
(Continued)

*Primary Examiner* — Lena Najarian
(74) *Attorney, Agent, or Firm* — Fish & Richardson P.C.

(57) ABSTRACT

Data from an information storage node of a service consortium blockchain is obtained. The information storage node is a blockchain node in the service consortium blockchain. The data from the information storage node of the service consortium blockchain is stored in a local database. A service processing request is received from a user device. The service processing request includes an identity of a user of the user device and service information of the user. The local database is searched for service data related to the user based on the identity of the user and the service information of the user. Based on the service data related to the user, service processing information to be used in a service processing operation performed responsive to the service processing request is determined. The service processing operation is completed for the user based on the service processing information.

27 Claims, 9 Drawing Sheets

(51) Int. Cl.
  *G16H 15/00* (2018.01)
  *G06F 16/23* (2019.01)

(56) References Cited

U.S. PATENT DOCUMENTS

| | | | |
|---|---|---|---|
| 2016/0217532 | A1 | 7/2016 | Slavin |
| 2016/0321751 | A1* | 11/2016 | Creighton, IV ....... G06Q 40/04 |
| 2017/0091173 | A1* | 3/2017 | Yao ....................... G06F 3/0488 |
| 2017/0177898 | A1* | 6/2017 | Dillenberger ....... G06F 16/2379 |
| 2018/0285979 | A1* | 10/2018 | Chessell ................ G06Q 40/08 |
| 2018/0337882 | A1* | 11/2018 | Li ........................... H04L 61/35 |
| 2019/0123580 | A1* | 4/2019 | Bindea .................. G05B 13/026 |
| 2019/0325115 | A1* | 10/2019 | Wilkinson .............. G06F 21/64 |
| 2019/0332608 | A1* | 10/2019 | Qiu ..................... G06F 16/2246 |

FOREIGN PATENT DOCUMENTS

| | | |
|---|---|---|
| CN | 108665946 | 10/2018 |
| CN | 109086325 | 12/2018 |
| CN | 109242699 | 1/2019 |
| CN | 109857797 A * | 6/2019 |
| TW | M568438 | 10/2018 |

OTHER PUBLICATIONS

Crosby et al., "BlockChain Technology: Beyond Bitcoin," Sutardja Center for Entrepreneurship & Technology Technical Report, Oct. 16, 2015, 35 pages.
Nakamoto, "Bitcoin: A Peer-to-Peer Electronic Cash System," www.bitcoin.org, 2005, 9 pages.
PCT International Search Report and Written Opinion in International Application No. PCT/US2020/013778, dated May 3, 2020, 14 pages.
PCT International Preliminary Reporton Patentability in International Application No. PCT/US2020/013778, dated Jul. 27, 2021, 8 pages.

\* cited by examiner

BLOCKCHAIN-BASED SERVICE PROCESSING

CROSS-REFERENCE TO RELATED APPLICATIONS

This application claims priority to Chinese Patent Application No. 201910059350.8, filed on Jan. 22, 2019, which is hereby incorporated by reference in its entirety.

TECHNICAL FIELD

The present application relates to the field of computer technologies, and in particular, to a blockchain-based service processing system and method, a computing device, and a storage medium.

BACKGROUND

With the growth of the economy, the quality of life and consumption of the masses are increasing, and more things have become important and even indispensable parts of our lives.

Taking insurance as an example, insurance has been integrated into people's lives as a guarantee mechanism. There are increasing types of insurance, and indemnity clauses of insurance are different. After purchasing insurance, a user can claim indemnity through insurance if an accident occurs within an insurance period.

At present, in a conventional indemnity process in the insurance industry, a to-be-processed user needs to provide relevant documents to the insurance company based on bills and certificates issued by the hospital. The insurance company determines whether the to-be-processed user satisfies claims based on the indemnity process and standard, and performs a subsequent claim settlement process after the claims are satisfied. For a to-be-processed user, claim reporting processes are complex, and various medical documents and receipts need to be provided. If the insurance company has any doubt as to whether the to-be-processed user satisfies claims, the to-be-processed user may need to go back to the hospital for document correction. In this case, it takes a long time from the start of reporting to completion of claim settlement, efficiency is low, and a service time is long, which seriously affects experience of an insured user. The insurance company needs to investigate the authenticity of various medical documents and receipts for a long time, which may result in low claim settlement efficiency. It is also difficult to identify whether investigators are cheating or not.

SUMMARY

In view of this, implementations of this specification provide a blockchain-based service processing system and method, a computing device, and a storage medium, to reduce technical defects in the existing technology.

According to one aspect, an implementation of this specification discloses a blockchain-based service processing system, including the following: a service consortium blockchain, a request client, and a server, where an information storage node corresponds to a blockchain node in the service consortium blockchain, and is configured to receive and store service data of a user, the server is configured to pull service data from a service consortium blockchain node, and store the service data in a local database, the request client is configured to send a service processing request to the server, where the service processing request includes an identity of the user and service information of the user, and the server is configured to receive the service processing request, search the local database for the service data related to the user based on the identity of the user and the service information of the user, determine information needed for service processing, and complete service processing for the user based on the information needed for service processing.

Optionally, the service consortium blockchain includes an insurance service consortium blockchain, an information storage node corresponds to a blockchain node in the insurance service consortium blockchain, and is configured to receive and store medical data of the user, the server is configured to pull data from an insurance service consortium blockchain node, and store the data in the local database, the request client is configured to send a case processing request to the server, where the case processing request includes the identity and medical visit information of the to-be-processed user, and the server is configured to receive the case processing request, search the local database for plan details and the medical data of the to-be-processed user based on the identity and the medical visit information of the to-be-processed user, determine information needed for case reporting based on the plan details and the medical data, and complete case processing for the user based on the information needed for case reporting.

Optionally, the server is further configured to send a service authorization request to the request client, the request client is further configured to receive the service authorization request and perform service authorization on the server, and the server is further configured to obtain a service authorization of the to-be-processed user, search for processing status information of the user based on the identity of the to-be-processed user, and if a processing status of the to-be-processed user is "being processed" or "processing completed", send a processing failure identifier to the request client, or if a processing status of the to-be-processed user is empty, search for plan details and the medical data of the to-be-processed user.

Optionally, the server is further configured to detect whether the to-be-processed user satisfies a predetermined processing condition based on medical visit information, plan details, and medical data of the user, and if the predetermined processing condition is satisfied, determine a to-be-indemnified amount corresponding to the to-be-processed user based on billing details in the medical visit information and an indemnity limit and an indemnity proportion corresponding to the billing details in the plan details, and perform a corresponding fast case processing operation based on the to-be-indemnified amount.

According to another aspect, an implementation of this specification discloses a blockchain-based service processing method, including the following: pulling data from a service consortium blockchain node and storing the data in a local database, receiving a service processing request of a to-be-processed user, where the service processing request includes an identity of the user and service information of the user, searching the local database for service data related to the user based on the identity of the user and the service information of the user, and determining information needed for service processing, and completing service processing for the user based on the information needed for service processing.

Optionally, the blockchain-based service processing method includes the following: pulling data from an insurance service consortium blockchain node and storing the data in the local database, receiving a case processing request of the to-be-processed user, where the case processing request includes the identity and medical visit information of the to-be-processed user, searching the local database for plan details and medical data of the to-be-processed user based on the identity and the medical visit information of the to-be-processed user, and determining information needed for case reporting based on the plan details and the medical data, and completing case processing for the user based on the information needed for case reporting.

Optionally, after the service processing request is received, the method further includes the following: sending a service authorization request to a request client, if a service authorization of the to-be-processed user is obtained, searching for processing status information of the to-be-processed user based on the identity of the to-be-processed user, and if a processing status of the to-be-processed user is "being processed" or "processing completed", sending a processing failure identifier to the request client, or if a processing status of the to-be-processed user is empty, searching for the service data of the to-be-processed user based on the identity of the user and the service information of the user.

Optionally, searching the local database for service data related to the user based on the identity of the user, and determining information needed for service processing includes the following: detecting whether the to-be-processed user satisfies a predetermined processing condition based on the service information, plan details, and the service data of the user, and if the to-be-processed user satisfies the predetermined processing condition, obtaining, from the service information based on the plan details, qualitative attribute information corresponding to a qualitative attribute of plan detail responsibility information, where the qualitative attribute information is the information needed for service processing.

Optionally, completing service processing for the user based on the information needed for service processing includes the following: calculating indemnity amounts corresponding to all items of service information based on an indemnity limit and an indemnity proportion in plan details matching the service information, and adding them up to obtain a total to-be-indemnified amount, comparing the to-be-indemnified amount with a maximum indemnity limit of the plan details, if the to-be-indemnified amount is less than or equal to the maximum indemnity limit, determining the to-be-indemnified amount as an indemnity amount of the to-be-processed user, or if the to-be-indemnified amount is greater than the maximum indemnity limit, determining the maximum indemnity limit as an indemnity amount of the to-be-processed user, and completing service processing for the user based on the indemnity amount.

According to another aspect, an implementation of this specification discloses a blockchain-based service processing apparatus, including the following: a pulling module, configured to pull data from a service consortium blockchain node and store the data in a local database, a receiving module, configured to receive a service processing request of a to-be-processed user, where the service processing request includes an identity of the user and service information of the user, a searching module, configured to search the local database for service data related to the user based on the identity of the user and the service information of the user, and determine information needed for service processing, and a processing module, configured to complete service processing for the user based on the information needed for service processing.

Optionally, the searching module includes the following: a sending submodule, configured to send a service authorization request to a request client, a first searching submodule, configured to: if a service authorization of the to-be-processed user is obtained, search for processing status information of the to-be-processed user based on the identity of the to-be-processed user, a determining submodule, configured to: if a processing status of the to-be-processed user is empty, search for plan details and the service data of the to-be-processed user, and determine whether the to-be-processed user satisfies a predetermined processing condition based on the service information, the plan details, and the service data of the user, and a second searching submodule, configured to: if the to-be-processed user satisfies the predetermined processing condition, obtain, from the service information based on the plan details, qualitative attribute information corresponding to a qualitative attribute of plan detail responsibility information, where the qualitative attribute information is the information needed for service processing.

Optionally, the processing module includes the following: a calculation submodule, configured to calculate indemnity amounts corresponding to all items of service information based on an indemnity limit and an indemnity proportion in plan details matching the service information, and add them up to obtain a total to-be-indemnified amount, and a determining submodule, configured to compare the to-be-indemnified amount with a maximum indemnity limit of the plan details to determine an actual indemnity amount of the to-be-processed user.

According to another aspect, an implementation of this specification discloses a computing device, including a memory, a processor, and a computer instruction that is stored in the memory and can run on the processor. When executing the instruction, the processor performs the steps of the blockchain-based service processing method.

According to another aspect, an implementation of this specification discloses a computer-readable storage medium, where the computer-readable storage medium stores a computer instruction, and a processor executes the instruction to perform the steps of the blockchain-based service processing method.

This specification provides a blockchain-based service processing system and method, the present disclosure expects to implement a fast consortium blockchain-based case processing method, because distributed accounting and storage are used in a blockchain, and there is no centralized hardware or management authority, and any nodes have equal rights and obligations, once information is verified and added to the blockchain, the information will be permanently stored, and modifying a database by a single node is invalid, Therefore, data is highly stable and highly reliable in the blockchain. In addition, a server directly searches a local database for related information after a user sends a case processing request, so that the user does not need to collect documents and receipts. As such, this is cost-effective and time-efficient, and user experience can be effectively improved.

DESCRIPTION OF IMPLEMENTATIONS

Many details are described in the following description to facilitate full understanding of this specification. However, this specification can be implemented in many different manners than those described herein. A person skilled in the art can perform similar promotion without violating the connotation of this specification. Therefore, this specification is not limited to the specific implementation disclosed below.

The term used in one or more implementations of this specification is merely for the purpose of describing a particular implementation and is not intended to limit one or more implementations of this specification. The terms "a" and "the" of singular forms used in one or more implementations of this specification and the appended claims are also intended to include plural forms, unless specified in the context clearly. It is further worthwhile to note that the term "and/or" used in one or more implementations of this specification indicates and includes any or all possible combinations of one or more associated listed items.

It is worthwhile to note that although terms "first", "second", etc. may be used in one or more implementations of this specification to describe various types of information, the information is not limited to the terms. These terms are only used to differentiate information of the same type. For example, without departing from the scope of one or more implementations of this specification, first can be referred to as second, and similarly, second can be referred to as first. Depending on the context, for example, the word "if" used here can be explained as "while", "when", or "in response to determining".

Terms in one or more implementations of the present disclosure are first explained.

Consortium blockchain: A plurality of preselected nodes are designated as bookkeepers in a group. Generation of each block is determined by the preselected nodes. Any other company and agency can perform restrictive access through APIs open to the blockchain.

This specification provides a blockchain-based service processing system and method, a computing device, and a storage medium, which are described in detail in the following implementations.

Figure 1:
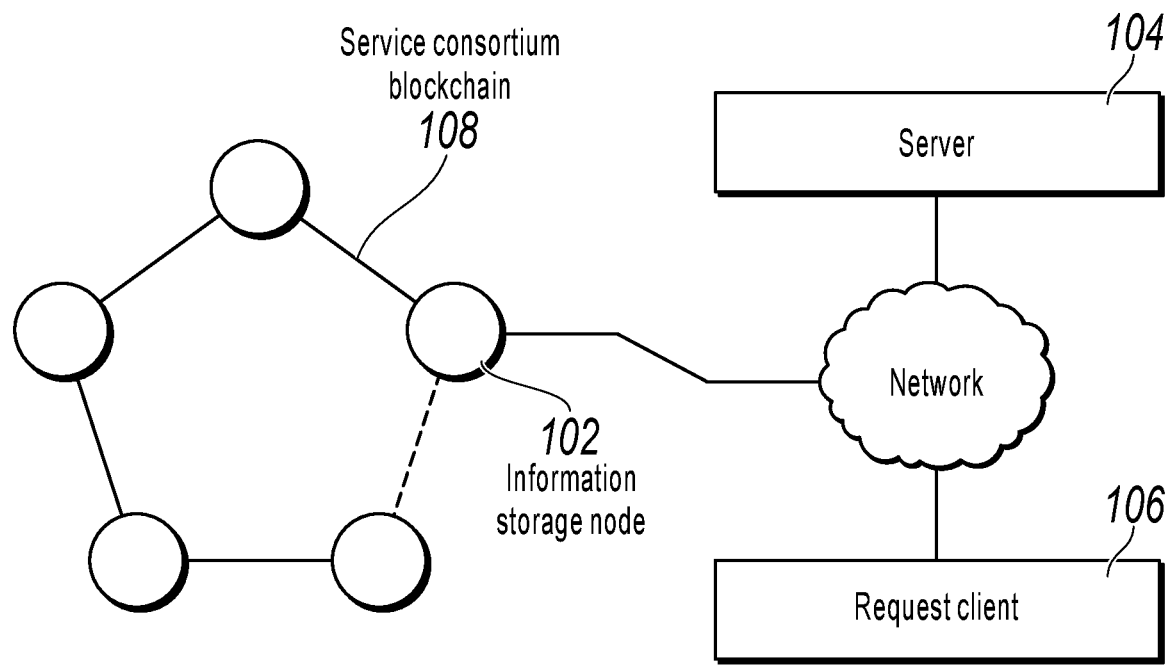
FIG. 1 is a schematic structural diagram illustrating a blockchain-based service processing system, according to an implementation of this specification.

FIG. 1 is a schematic structural diagram illustrating a blockchain-based service processing system, according to an implementation of this specification. The service processing system includes the following: an information storage node 102, a server 104, a request client 106, and a service consortium blockchain 108. The service consortium blockchain 108 is used as a blockchain for information storage in this specification.

The information storage node 102 corresponds to a blockchain node in the service consortium blockchain, and is configured to receive and store service data of a user.

In one or more implementations of this specification, the service consortium blockchain can be an insurance service consortium blockchain, an assistance service consortium blockchain, etc.

The server 104 is configured to pull service data from a service consortium blockchain node, and store the service data in a local database.

The request client 106 is configured to send a service processing request to the server, where the service processing request includes an identity of the user and service information of the user.

The server 104 is further configured to receive the service processing request, search the local database for the service data related to the user based on the identity of the user and the service information of the user, determine information needed for service processing, and complete service processing for the user based on the information needed for service processing.

The server 104 is further configured to send service processing status information to the service consortium blockchain node.

The service consortium blockchain 108 is further configured to receive the service processing status information.

In one or more implementations of this specification, network nodes in the service consortium blockchain include a service-related agency node, a device node of a regulatory agency, and a service device of an Internet platform accessing the blockchain.

Different services involve different agencies, and therefore, service-related agency device nodes in different service consortium blockchains are also different. For example, a service-related agency device node corresponding to financial insurance can include a maintenance factory, a third-party assessment agency, etc. A service-related agency device node corresponding to medical insurance can include a medical terminal device node, a service device node of a medical service agency, etc. This is determined based on a specific situation in actual applications, and implementations are not limited in this specification.

The following uses medical insurance as an example for description. In a medical insurance service, information storage node 1 is disposed on a medical terminal device node, information storage node 2 is disposed on a service device node of a medical service agency, information storage node 3 is disposed on a service device node of an Internet platform, etc. The information storage nodes 1 to 3 are not necessarily disposed on blockchain nodes in a service consortium blockchain, and can be disposed on independent nodes other than the blockchain nodes.

In one or more implementations of this specification, members in the blockchain include a regulatory agency, a service processing related agency, etc. The consortium blockchain is used for data storage, and is monitored by the regulatory agency to ensure that stored service data of a user is not tampered with. The server pulls data from the blockchain. After the user sends a service processing request, the server can directly search the local database for related data, and no investigation on the authenticity and accuracy of service data is needed. In addition, the user does not need to collect service data repeatedly. As such, service processing can be completed quickly, and is more time-efficient.

Figure 2:
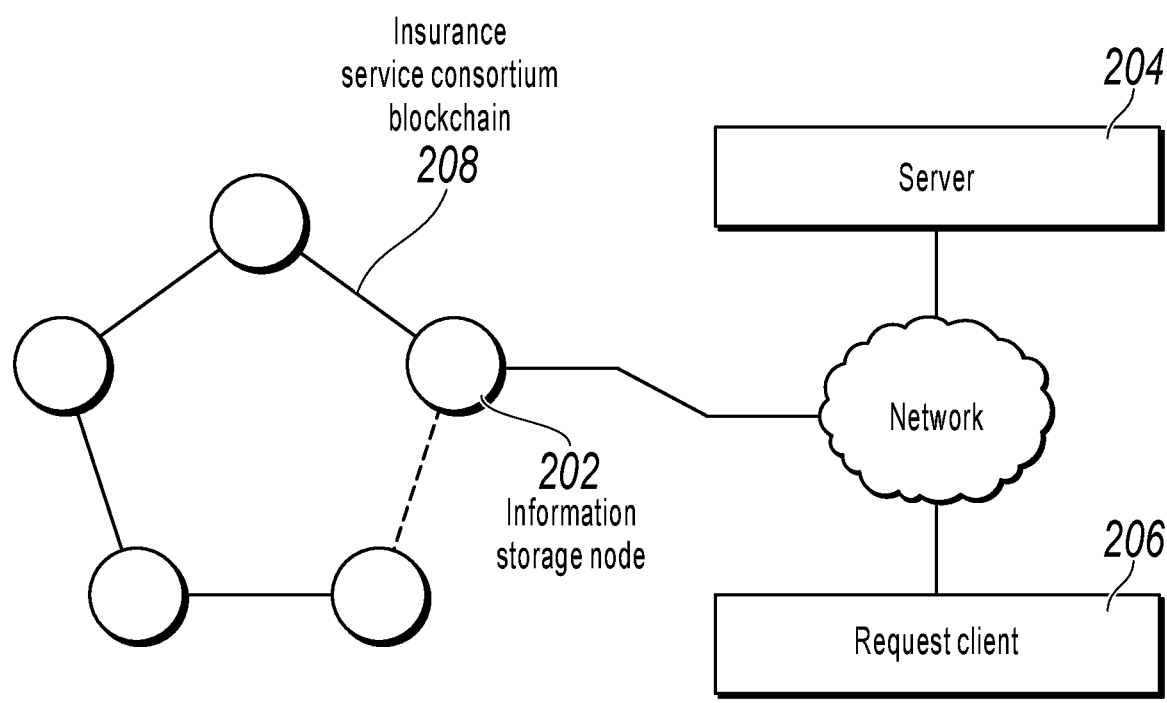
FIG. 2 is a schematic structural diagram illustrating a blockchain-based service processing system, according to an implementation of this specification.

FIG. 2 is a schematic structural diagram illustrating a blockchain-based service processing system, according to an implementation of this specification. The service processing system includes the following: an information storage node 202, a server 204, a request client 206, and an insurance service consortium blockchain 208. The insurance service consortium blockchain 208 is used as a blockchain for information storage in this specification.

The information storage node 202 corresponds to a blockchain node in the insurance service consortium blockchain, and is configured to receive and store medical data of a user.

The server 204 is configured to pull data from an insurance service consortium blockchain node, and store the data in a local database.

The request client 206 is configured to send a case processing request to the server, where the case processing request includes an identity and medical visit information of the to-be-processed user.

The server 204 is further configured to receive the case processing request, search the local database for plan details and the medical data of the to-be-processed user based on the identity and the medical visit information of the to-be-processed user, determine information needed for case reporting based on the plan details and the medical data, and complete case processing for the user based on the information needed for case reporting.

The server 204 is further configured to send processing status information to the service consortium blockchain node.

The insurance service consortium blockchain 208 is further configured to receive the processing status information.

In one or more implementations of this specification, the insurance service consortium blockchain 208 includes a service-related agency device node, a service device node of an Internet platform, a device node of a regulatory agency, and a service device node of an insurance agency accessing the blockchain.

The following uses medical insurance as an example for description. In a medical insurance service, information storage node 1 is disposed on a device node of a regulatory agency, information storage node 2 is disposed on a service device node of an insurance agency, information storage node 3 is disposed on a service device node of an Internet platform, etc. The information storage nodes 1 to 3 are not necessarily disposed on blockchain nodes in an insurance service consortium blockchain, and can be disposed on independent nodes other than the blockchain nodes.

In one or more implementations of this specification, members in the insurance service consortium blockchain include a regulatory agency, an insurance company, a medical service related agency, etc. The consortium blockchain is used for data storage, and is monitored by the regulatory agency to ensure that stored visit data of a user is not tampered with. The medical agency uploads the visit data of the user to a consortium blockchain node, and the server pulls the data from the consortium blockchain node. After the user sends a case processing request, the server can directly search the local database for related data, and no investigation on the authenticity and accuracy of visit data is needed. As such, service processing can be completed quickly, and is more time-efficient.

Figure 3:
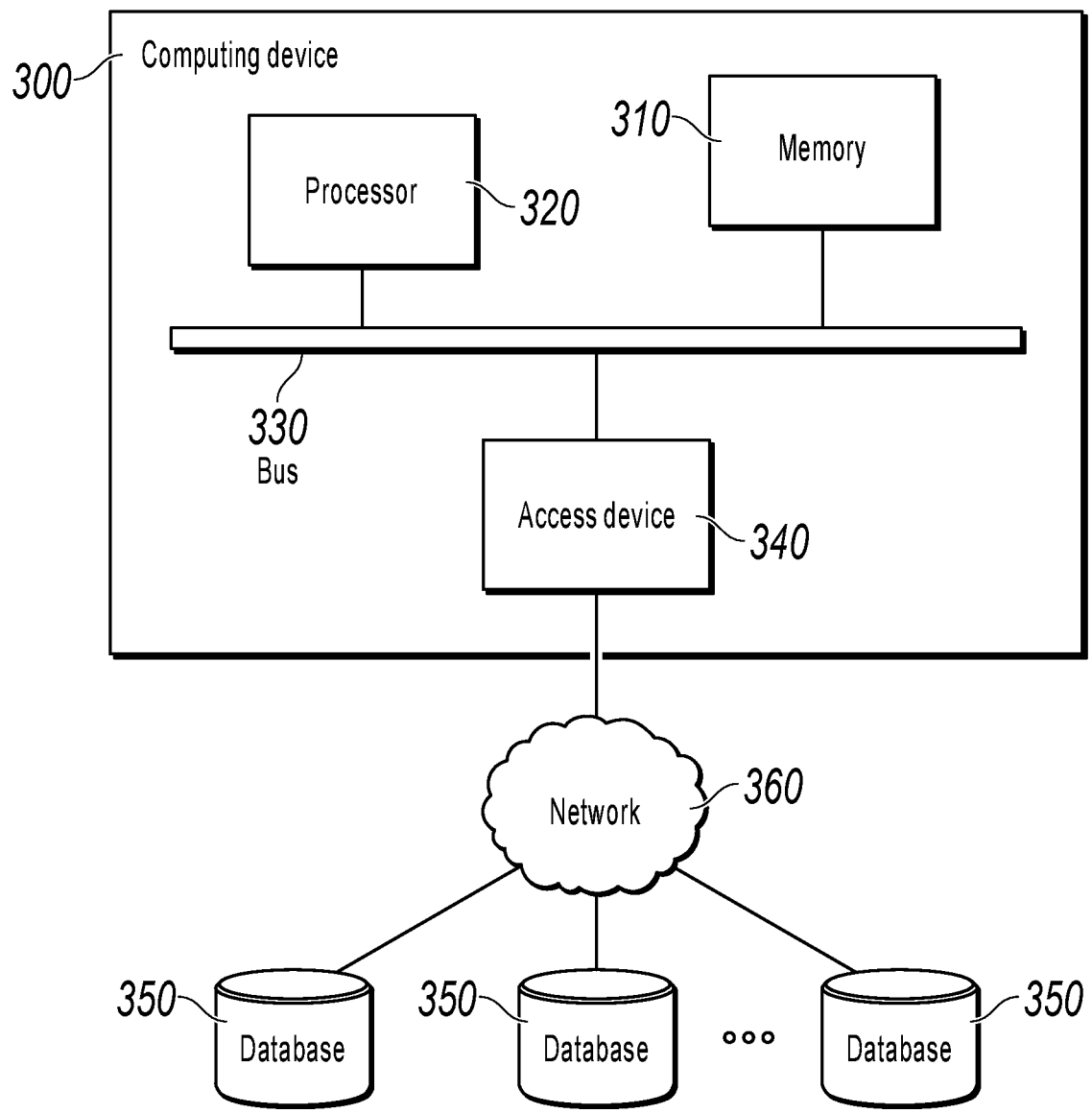
FIG. 3 is a structural block diagram illustrating a computing device, according to an implementation of this specification.

FIG. 3 is a structural block diagram illustrating a computing device 300, according to an implementation of this specification. Components of the computing device 300 include but are not limited to a memory 310 and a processor 320. The processor 320 and the memory 310 are connected to each other by using a bus 330.

The computing device 300 further includes an access device 340. The access device 340 can include one or more wired or wireless network interfaces of any type (e.g., a network interface card (NIC)), for example, an IEEE 802.11 wireless local area network (WLAN) wireless interface, a Worldwide Interoperability for Microwave Access (WiMAX) interface, an Ethernet interface, a Universal Serial Bus (USB) interface, a cellular network interface, a Bluetooth interface, and a Near Field Communication (NFC) interface.

In an implementation of this specification, the foregoing components of the computing device 300 and other components not shown in FIG. 3 can also be connected to each other, for example, by using the bus. It is worthwhile to note that the structural block diagram of the computing device shown in FIG. 3 is merely used as an example, and does not impose a limitation on the scope of this specification. A person skilled in the art can add or replace a component as required.

The computing device 300 can be any type of stationary or mobile computing device, including a mobile computer or a mobile computing device (e.g., a tablet computer, a personal digital assistant, a laptop computer, a notebook computer, or a netbook), a mobile phone (e.g., a smartphone), a wearable computing device (e.g., a smartwatch or smart glasses), another type of mobile device, or a stationary computing device such as a desktop computer or a PC. Alternatively, the computing device 300 can be a mobile or stationary server.

Figure 4:
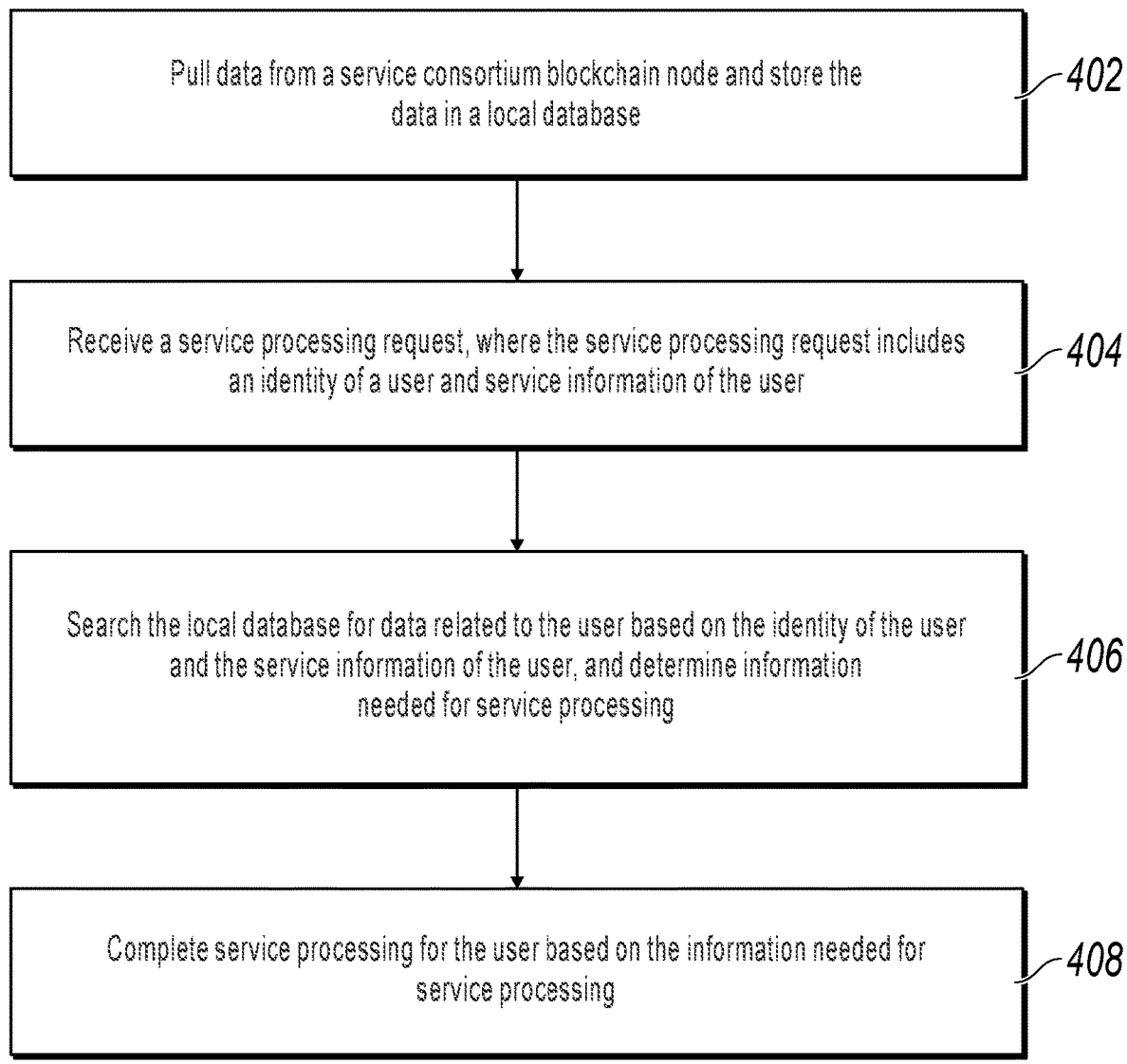
FIG. 4 is a flowchart illustrating a blockchain-based service processing method, according to an implementation of this specification.

The processor 320 can perform steps of a method shown in FIG. 4. FIG. 4 is a flowchart illustrating a blockchain-based service processing method, according to an implementation of this specification. The method is applied to a server, and includes step 402 to step 408.

Step 402: Pull data from a service consortium blockchain node and store the data in a local database.

In one or more implementations of this specification, the server pulls data from a blockchain node in two ways: an active pull mode and a monitor pull mode. The active pull mode means pulling node data in a blockchain at intervals and writing the node data to the local database. The monitor pull mode means monitoring block information of the blockchain, pulling node data, and writing the node data to the local database. In a data pulling process, block data pulled each time is determined by a block height. For example, if 10000 blocks numbered 1 to 10000 have been pulled, and the block height increases to 10100 after a period of time, only information of 100 newly added blocks from 10000 to 10100 are pulled, so that data can be effectively prevented from being pulled repeatedly.

Step 404: Receive a service processing request, where the service processing request includes an identity of a user and service information of the user.

In an implementation of this specification, the service processing request includes an insurance claim request, an assistance insurance service request, etc. The insurance claim request is used as an example. When sending a case processing request, the user needs to fill in related information, including a name, a visit type, a phone number, a visit city, a visit hospital, and a visit time.

Step 406: Search the local database for data related to the user based on the identity of the user and the service information of the user, and determine information needed for service processing.

Step 408: Complete service processing for the user based on the information needed for service processing.

In one or more implementations of this specification, the server locally searches for the data related to the user based on the identity and the service information of the user, and then obtains information that satisfies a predetermined processing condition from the data, so that the user does not need to repeatedly collect and upload related service information, thereby effectively improving service processing efficiency.

Figure 5:
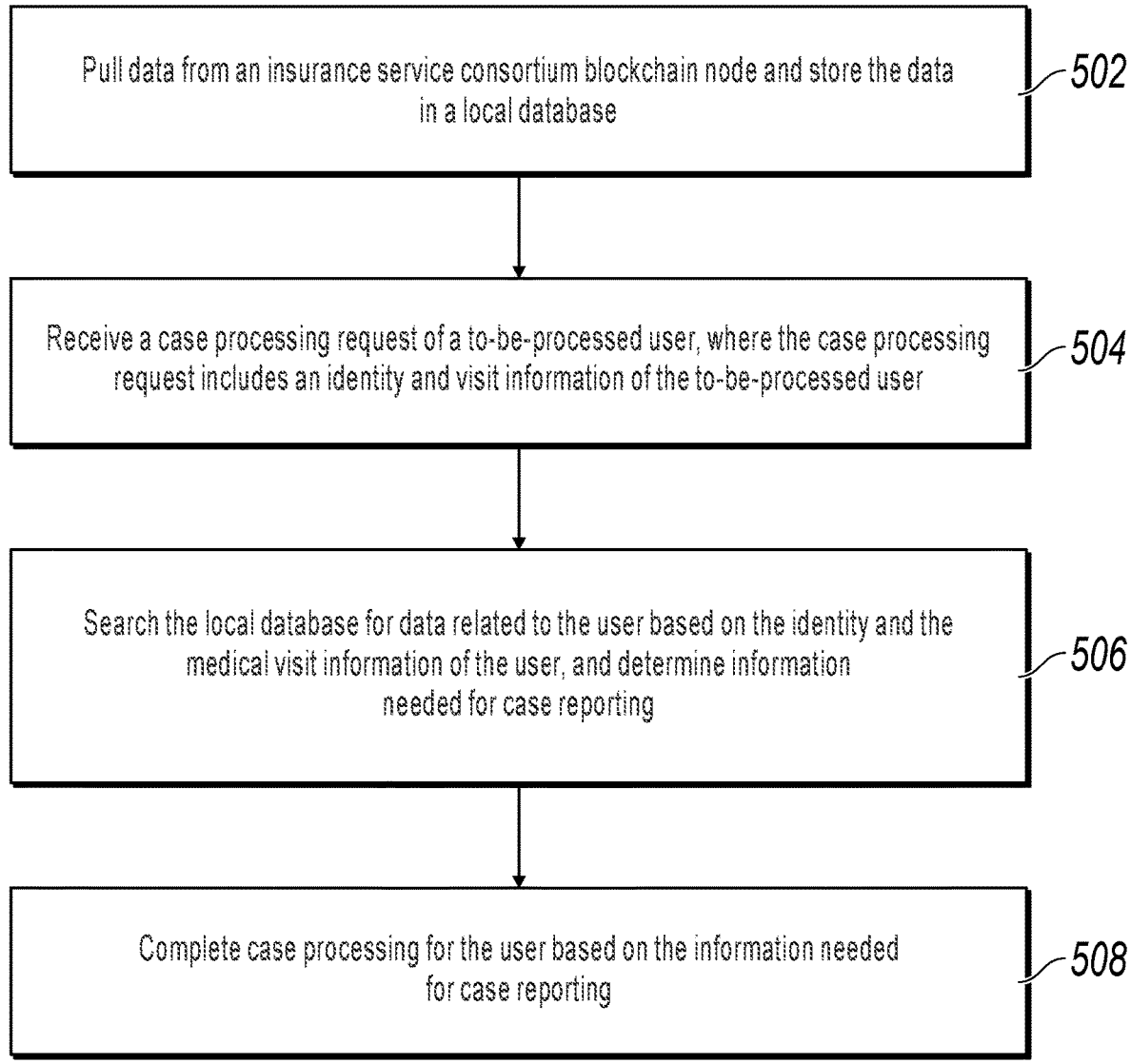
FIG. 5 is a flowchart illustrating a blockchain-based service processing method, according to an implementation of this specification.

The following uses an insurance service as an example to describe a service processing method provided in this specification. In this implementation, the service processing method is described with reference to FIG. 5 by using information storage node 1 on a blockchain node in an insurance service consortium blockchain. The service processing method is applied between an insurance service consortium blockchain, a server, and a request client. As shown in FIG. 5, the service processing method can include step 502 to step 508.

Step 502: Pull data from an insurance service consortium blockchain node and store the data in a local database.

Before the server pulls the data from the blockchain node, a medical agency uploads medical visit information of a user to a closest blockchain node based on a predetermined data model. The predetermined data model is shown in Table 1.

pull mode means monitoring block information of the blockchain, pulling node data, and writing the node data to the local database. In a data pulling process, block data pulled each time is determined by a block height. For example, if 10000 blocks numbered 1 to 10000 have been pulled, and the block height increases to 10100 after a period of time, only information of 100 newly added blocks from 10000 to 10100 are pulled, so that data can be effectively prevented from being pulled repeatedly.

Step 504: Receive a case processing request of the to-be-processed user, where the case processing request includes an identity of the user and medical visit information of the user.

In an implementation of this specification, when sending the case processing request, the user needs to fill in related information, including a name, a visit type, a phone number, a visit city, a visit hospital, and a visit time.

The following uses an example that Lily applies for claim settlement for description. Related information filled in to send a claim settlement request is shown in Table 2.

TABLE 1

| Field | Name of the field | Data type | Data constraint | Data sample | Data remarks |
|---|---|---|---|---|---|
| HOSPITAL_CODE | Hospital code | C | Non-empty | Z000001 | Fixed value, as defined upon the start of the item |
| VISIT_DATE | Visit date | D | Non-empty | 2018 Jan. 5 15:05:30 | In the format of date, accurate to seconds |
| NAME | Name | C | Non-empty | Sophie | Patient name |
| ID_NO | ID number | C | Non-empty | 620503xxx XXX | It is an ID card number by default, is non-empty, and requires strong verification |
| VISIT_DEPT_NAME | Visit department name | C | Non-empty | Endocrine department | Actually visited department, not a registered or reserved department |
| DOCTOR_CODE | Doctor code | C | Can be empty | 1000067 | |
| DOCTOR_NAME | Doctor name | C | Can be empty | Alice | |

Only a few pieces of important information are listed in the previous table. There is one visit record each time a patient pays a visit to an outpatient clinic. The record further includes information such as a unique identification number, a visit serial number, a visit type, a medical insurance card number, a certificate type name, and a visit department code.

In one or more implementations of this specification, the server pulls data from a blockchain node in two ways: an active pull mode and a monitor pull mode. The active pull mode means pulling node data in a blockchain at intervals and writing the node data to the local database. The monitor

TABLE 2

| Application form | |
|---|---|
| Applicant name | Lily |
| Visit city | Beijing |
| Visit type | Inpatient |
| Visit hospital | Beijing *** Hospital |
| Visit time | 2018 Dec. 3 to 2018 Jan. 3 |
| Phone number | 152******** |

Only a few pieces of important information are listed in the previous table. In addition to the information in the previous table, other related information may need to be filled in when a patient sends a claim settlement request.

Step 506: Search the local database for data related to the user based on the identity and the medical visit information of the user, and determine information needed for case reporting.

Step 508: Complete case processing for the user based on the information needed for case reporting.

In one or more implementations of this specification, based on a settlement result of the reporting information, a corresponding quantity of virtual resources are deducted from an account address where the server registers with an application system, and a corresponding quantity of virtual resources are transferred to an account address where the user registers with the application system.

In one or more implementations of this specification, the server locally searches for the data, including plan details and medical data, related to the user based on the identity of the user, and then obtains information that satisfies a predetermined processing condition from the data, so that case processing efficiency is effectively improved.

Figure 6:
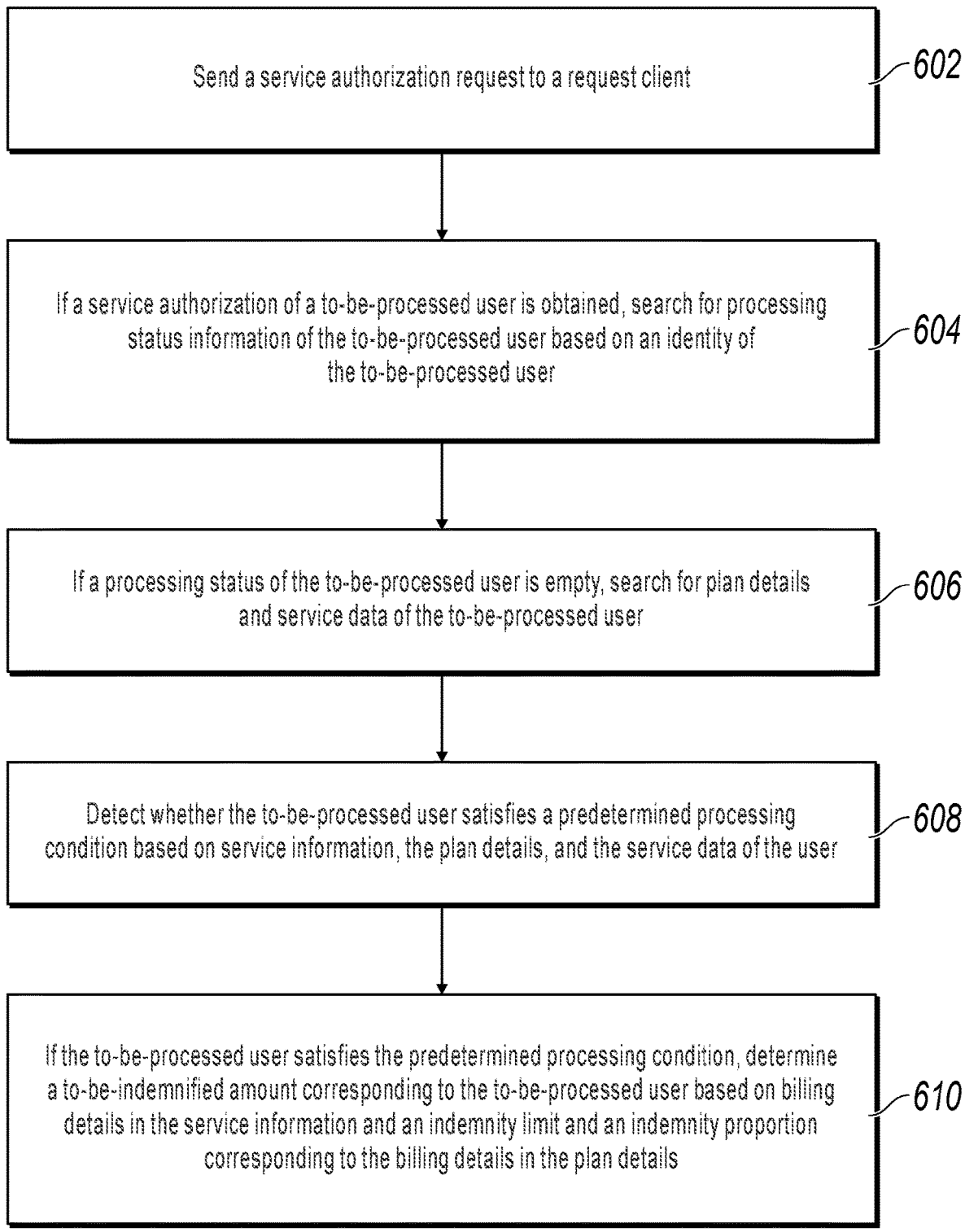
FIG. 6 is a flowchart illustrating a blockchain-based service processing method, according to an implementation of this specification.

FIG. 6 is a flowchart illustrating a blockchain-based service processing method, according to an implementation of this specification. The method includes step 602 to step 610.

Step 602: Send a service authorization request to a request client.

In an implementation of the present disclosure, after a user authorizes a server, the server can search for related information of the user.

Step 604: If a service authorization of the to-be-processed user is obtained, search for processing status information of the to-be-processed user based on an identity of the to-be-processed user.

In an implementation of the present disclosure, the processing status information of the user is uploaded from the server to a blockchain. The processing status information of the user is first searched for to determine whether the user has sent a case processing request to another server or case processing is completed. If a processing status of the user is "being processed" or "processing completed", a processing failure identifier is sent to the request client.

Step 606: If the processing status of the to-be-processed user is empty, search for plan details and service data of the to-be-processed user.

Step 608: Detect whether the to-be-processed user satisfies a predetermined processing condition based on service information, the plan details, and the service data of the user.

The server determines responsibility information corresponding to the plan details based on the plan details, obtains a qualitative attribute corresponding to the responsibility information, and obtains qualitative attribute information corresponding to the qualitative attribute from service information in a database based on the plan details. When identifying fully matched scenario data, the server considers that the user satisfies one of predetermined processing conditions, and further needs to perform determining based on another condition. When the server cannot identify fully matched scenario data, the server sends a matching failure notification to the user, where the notification information is "You have no insurance on the currently applied item".

The following uses a user as an example for description. Assume that the user purchases major disease insurance, and medical visit information included in a case processing request includes "myocardial infarction inpatient" and "fracture inpatient". Based on a disease type table, it can be seen that a disease type of myocardial infarction is a major disease and a fracture is an accidental injury disease. Therefore, it can be preliminarily determined that "myocardial infarction inpatient" in the medical visit information of the user satisfies one of predetermined processing conditions. In addition, further determining needs to be performed based on another condition. For example, to ensure security of a claim operation and reduce a claim risk of the insurance company, some user information about a violation record or behaviors such as cheating can be pre-stored in a claim blacklist. When whether a to-be-processed user satisfies a predetermined claim condition is being determined, it can be determined whether the user is in the blacklist. If the user is in the claim blacklist, there is a high risk in performing a claim operation for the user, and the user does not satisfy the predetermined claim condition. If the user is not in the blacklist, but the user requests for many insurance claims in recent half month, it indicates that the user frequently claims insurance recently, and therefore, the user may be a fraud, and it can be determined that the user does not satisfy the predetermined claim condition, to ensure security of the claim operation.

Step 610: If the to-be-processed user satisfies the predetermined processing condition, determine a to-be-indemnified amount corresponding to the to-be-processed user based on billing details in the service information and an indemnity limit and an indemnity proportion corresponding to the billing details in the plan details.

In one or more implementations of this specification, indemnity amounts corresponding to all items of service information are calculated based on an indemnity limit and an indemnity proportion in plan details matching the service information, and the indemnity amounts are added up to obtain a total to-be-indemnified amount. The to-be-indemnified amount is compared with a maximum indemnity limit of the plan details. If the to-be-indemnified amount is less than or equal to the maximum indemnity limit, the to-be-indemnified amount is determined as an indemnity amount of the to-be-processed user, or if the to-be-indemnified amount is greater than the maximum indemnity limit, the maximum indemnity limit is determined as an indemnity amount of the to-be-processed user.

The server calculates indemnity amounts for all bills based on the plan details of the to-be-processed user, the billing details in the service information, and the indemnity limit and the indemnity proportion corresponding to the billing details in the plan details, and adds them up to obtain a total to-be-indemnified amount. A maximum indemnity limit of each product can be determined based on content of the plan details.

For example, if medical visit information of the to-be-processed user includes a hospital medical fee, a hospital bed fee, and a hospital operation fee, a medical policy of the user is searched for responsibility details of the three expenses, to identify indemnity proportions and indemnity limits of the three expenses. Finally, an indemnity amount corresponding to the user is calculated.

In one or more implementations of this specification, the server needs to search for related data of the user after obtaining the service authorization of the user. After being authorized, the server first determines whether the processing status of the user is "being processed" or "processing completed", to effectively reduce repeated processing. The server determines whether the medical visit information of the user matches the scope of the policy, to determine whether the user is in the claim blacklist, so that claim security can be effectively improved.

Figure 7:
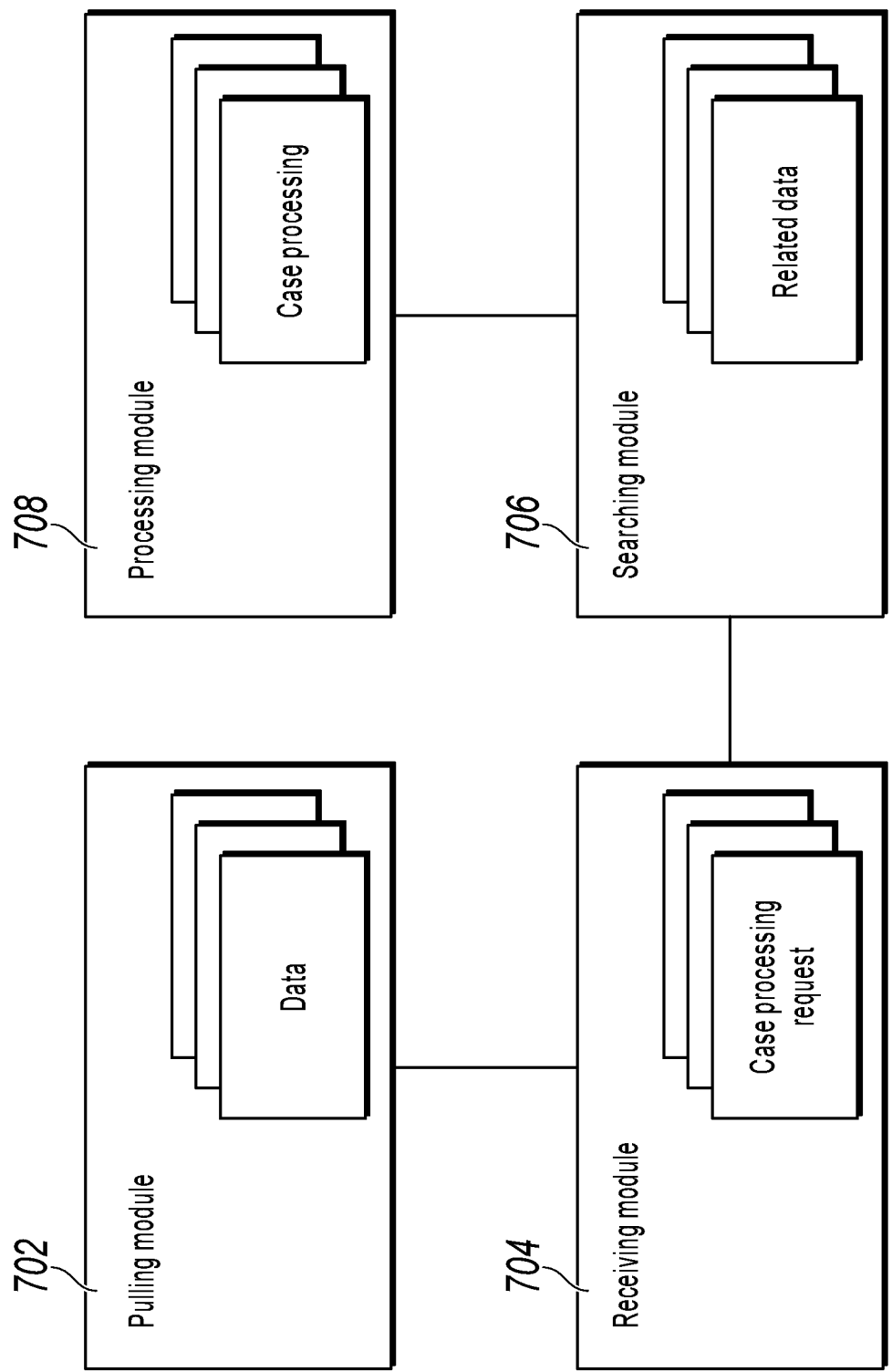
FIG. 7 is a schematic structural diagram illustrating a blockchain-based service processing apparatus, according to an implementation of this specification.

An implementation of this specification further provides a blockchain-based service processing apparatus. As shown in FIG. 7, the apparatus includes a pulling module 702, a receiving module 704, a searching module 706, and a processing module 708.

The pulling module 702 is configured to pull data from a service consortium blockchain node and store the data in a local database.

In one or more implementations of this specification, an insurance service is used as an example. Before a server pulls the data from the blockchain node, a medical agency uploads medical visit information of a user to a closest blockchain node based on a predetermined data model.

In one or more implementations of this specification, the server pulls data from a blockchain node in two ways: an active pull mode and a monitor pull mode. The active pull mode means pulling node data in a blockchain at intervals and writing the node data to the local database. The monitor pull mode means monitoring block information of the blockchain, pulling node data, and writing the node data to the local database. In a data pulling process, block data pulled each time is determined by a block height. For example, if 10000 blocks numbered 1 to 10000 have been pulled, and the block height increases to 10100 after a period of time, only information of 100 newly added blocks from 10000 to 10100 are pulled, so that data can be effectively prevented from being pulled repeatedly.

The receiving module 704 is configured to receive a service processing request of the to-be-processed user, where the service processing request includes an identity of the user and service information of the user.

The insurance service is still used as an example. When sending a case processing request, the user needs to fill in related information, including a name, a visit type, a phone number, a visit city, a visit hospital, and a visit time.

The searching module 706 is configured to search the local database for service data related to the user based on the identity of the user and the service information of the user, and determine information needed for service processing.

The processing module 708 is configured to complete service processing for the user based on the information needed for service processing.

In one or more implementations of this specification, based on a settlement result, a corresponding quantity of virtual resources are deducted from an account address where the server registers with an application system, and a corresponding quantity of virtual resources are transferred to an account address where the user registers with the application system.

In one or more implementations of this specification, the server locally searches for the data, including plan details and service data, related to the user based on the identity of the user, and then obtains information that satisfies a predetermined processing condition from the data. Through comparison based on a plurality of conditions, security is effectively improved.

Figure 8:
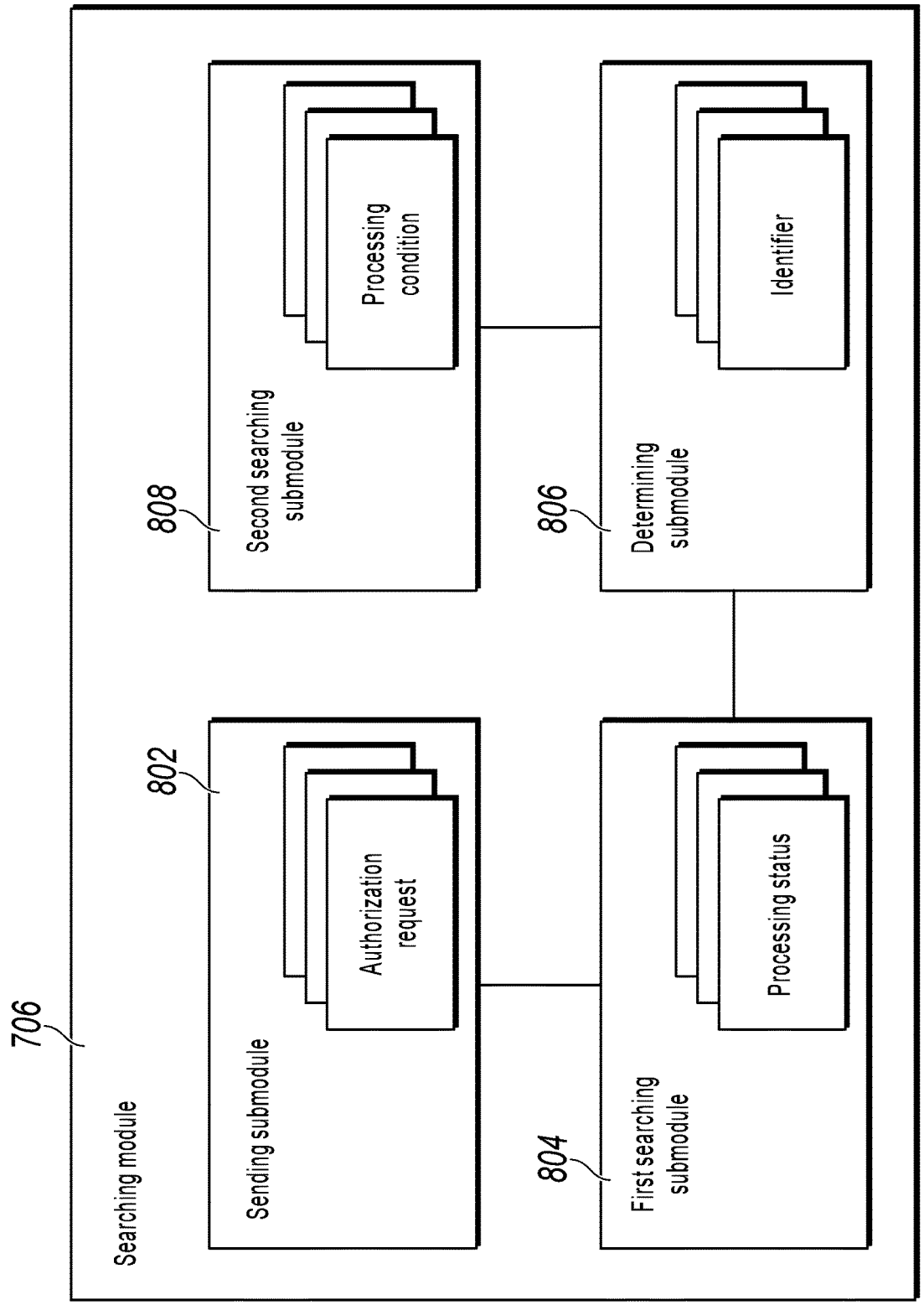
FIG. 8 is a schematic structural diagram illustrating a blockchain-based service processing apparatus, according to an implementation of this specification.

An implementation of this specification further provides a blockchain-based service processing apparatus. As shown in FIG. 8, the searching module 706 includes a sending submodule 802, a first searching submodule 804, a determining submodule 806, and a second searching submodule 808.

The sending submodule 802 is configured to send a service authorization request to a request client.

In an implementation of the present disclosure, after the user authorizes the server, the server can search for related information of the user.

The first searching submodule 804 is configured to: if a service authorization of the to-be-processed user is obtained, search for processing status information of the to-be-processed user based on the identity of the to-be-processed user.

In an implementation of the present disclosure, the processing status information of the user is uploaded from the server to a blockchain. The processing status information of the user is first searched for to determine whether the user has sent a case processing request to another server or case processing is completed. If a processing status of the user is "being processed" or "processing completed", a processing failure identifier is sent to the request client.

The determining submodule 806 is configured to: if a processing status of the to-be-processed user is empty, search for plan details and the service data of the to-be-processed user, and determine whether the to-be-processed user satisfies a predetermined processing condition based on the service information, the plan details, and medical data of the user.

The server determines responsibility information corresponding to the plan details based on the plan details, obtains a qualitative attribute corresponding to the responsibility information, and obtains qualitative attribute information corresponding to the qualitative attribute from service information in a database based on the plan details. When identifying fully matched scenario data, the server considers that the user satisfies one of predetermined processing conditions, and further needs to perform determining based on another condition. When the server cannot identify fully matched scenario data, the server sends a matching failure notification to the user, where the notification information is "You have no insurance on the currently applied item".

The second searching submodule 808 is configured to: if the to-be-processed user satisfies the predetermined processing condition, obtain, from the service information based on the plan details, qualitative attribute information corresponding to a qualitative attribute of plan detail responsibility information, where the qualitative attribute information is the information needed for service processing.

In one or more implementations of this specification, if the processing status of the user is "being processed" or "processing completed", or the user does not satisfy the predetermined processing condition, the processing failure identifier is sent to the request client, to effectively improve security.

Figure 9:
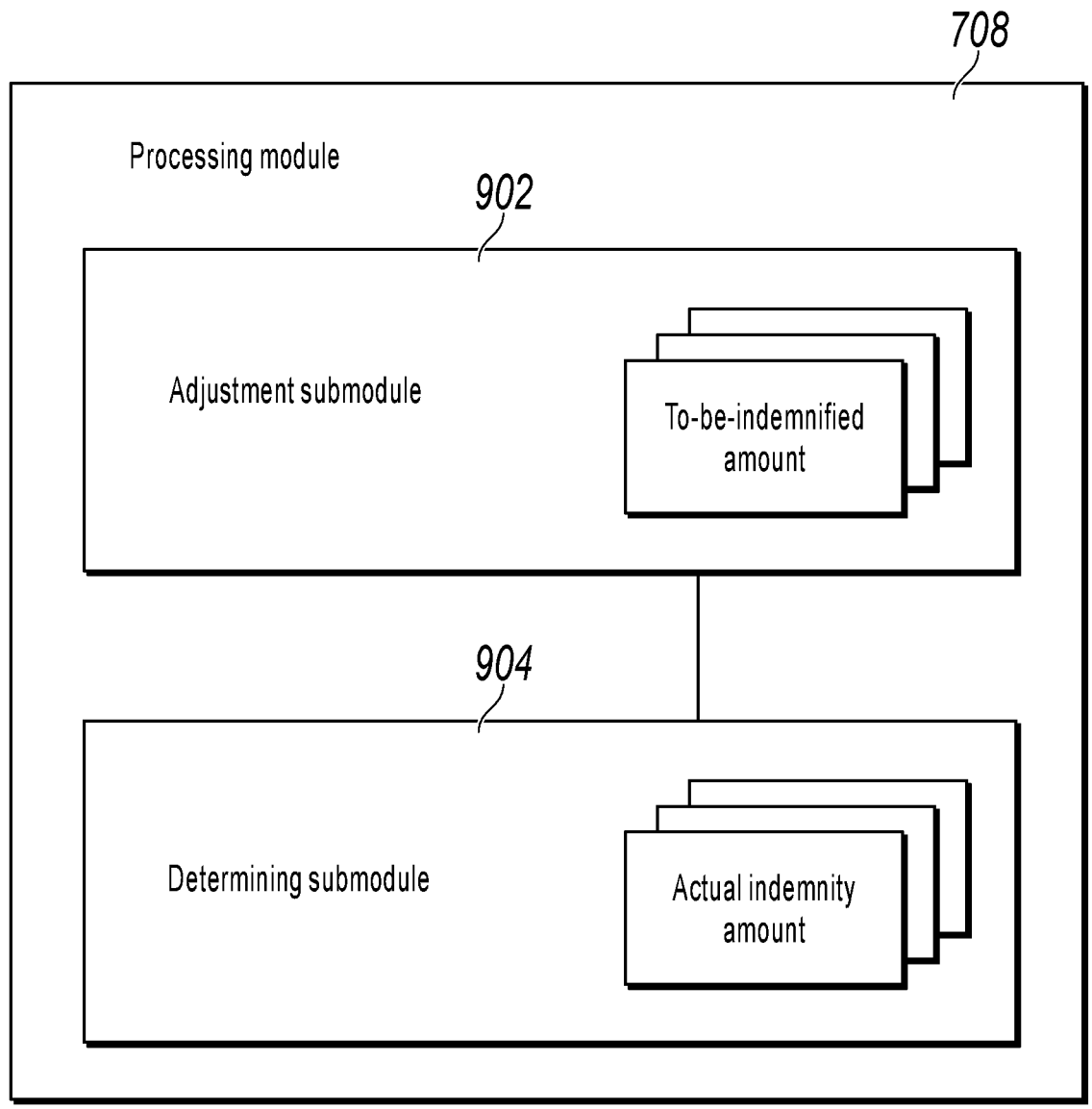
FIG. 9 is a schematic structural diagram illustrating a blockchain-based service processing apparatus, according to an implementation of this specification.

An implementation of this specification further provides a blockchain-based service processing apparatus. As shown in FIG. 9, the processing module 708 includes a calculation submodule 902 and a determining submodule 904.

The calculation submodule 902 is configured to calculate indemnity amounts corresponding to all items of service information based on an indemnity limit and an indemnity proportion in plan details matching the service information, and add them up to obtain a total to-be-indemnified amount.

In one or more implementations of this specification, the insurance service is still used as an example. Indemnity amounts corresponding to all items of medical visit information are calculated based on an indemnity limit and an indemnity proportion in plan details matching the medical visit information, and the indemnity amounts are added up to obtain a total to-be-indemnified amount. The to-be-indemnified amount is compared with a maximum indemnity limit of the plan details. If the to-be-indemnified amount is less than or equal to the maximum indemnity limit, the to-be-indemnified amount is determined as an indemnity amount of the to-be-processed user; or if the to-be-indemnified amount is greater than the maximum indemnity limit, the maximum indemnity limit is determined as an indemnity amount of the to-be-processed user.

The server calculates indemnity amounts for all items based on the plan details of the to-be-processed user, billing details in the medical visit information, and the indemnity limit and the indemnity proportion corresponding to the billing details in the plan details, and adds them up to obtain a total to-be-indemnified amount. A maximum indemnity limit of each medical insurance product can be determined based on policy content.

The determining submodule 904 is configured to compare the to-be-indemnified amount with a maximum indemnity limit of the plan details to determine an actual indemnity amount of the to-be-processed user.

In one or more implementations of this specification, if the to-be-indemnified amount is less than or equal to the maximum indemnity limit, the to-be-indemnified amount is determined as an indemnity amount of the to-be-processed user, or if the to-be-indemnified amount is greater than the maximum indemnity limit, the maximum indemnity limit is determined as an indemnity amount of the to-be-processed user.

In one or more implementations of this specification, service data of a user is stored by using a service consortium blockchain, to ensure that data is not tampered with. A server pulls data from a consortium blockchain node. If the user needs to perform service processing, the user only needs to submit an application in an application system, and the system directly searches a local database for data related to the user, without requiring the user to provide paper bills and proofs. Because data stored in the consortium blockchain cannot be tampered with, when determining whether a to-be-processed user satisfies a predetermined processing condition, the server does not need to investigate the authenticity of various user data. As such, the time needed from the start of case reporting to completion of the processing is much shorter, and processing efficiency is improved.

An implementation of the present application further provides a computing device, including a memory, a processor, and a computer instruction that is stored in the memory and can run on the processor. When executing the instruction, the processor performs the steps of the blockchain-based service processing method. An implementation of the present application further provides a computer-readable storage medium, where the computer-readable storage medium stores a computer instruction, and a processor executes the instruction to perform the steps of the blockchain-based service processing method.

The previous description is an example solution of the computer-readable storage medium in this implementation. It is worthwhile to note that the technical solution of the storage medium and the technical solution of the blockchain-based service processing method belong to a same concept. For details not described in detail in the technical solution of the storage medium, references can be made to the description of the technical solution of the blockchain-based service processing method.

The computer instruction includes computer program code, and the computer program code can be source code, object code, an executable file, some intermediate forms, etc. The computer-readable medium can include any entity or apparatus, a recording medium, a USB flash drive, a removable hard disk, a magnetic disk, an optical disc, a computer memory, a read-only memory (ROM), a random access memory (RAM), an electrical carrier signal, a telecommunications signal, a software distribution medium, etc. that can carry the computer program code. It is worthwhile to note that content included in the computer-readable medium can be appropriately increased or decreased based on a requirement of legislation and patent practice in a jurisdiction. For example, in some jurisdictions, according to legislation and patent practice, the computer-readable medium does not include an electrical carrier signal and a telecommunications signal.

It is worthwhile to note that to make the description brief, the previous method implementations are expressed as a combination of a series of actions. However, a person skilled in the art should appreciate that this specification is not limited to the described action sequence because some steps can be performed in other sequences or performed simultaneously according to this specification. In addition, a person skilled in the art should also appreciate that all the implementations described in this specification are examples of implementations, and the actions and modules mentioned are not necessarily mandatory to this specification.

In the previous implementations, the description of each implementation has respective focuses. For a part not described in detail in an implementation, references can be made to related descriptions in other implementations.

The examples of implementations of this specification disclosed above are merely intended to help describe this specification. The optional implementations do not describe all details in detail, and the present disclosure is not limited to the specific implementations. Obviously, many modifications and changes can be made based on the content of this specification. These implementations are selected and described in detail in this specification to better explain principles and practical applications of the present application, so that a person skilled in the art can better understand and use the present application. This specification is limited only by the claims and all the scope and equivalents thereof.

What is claimed is:

1. A computer-implemented method, comprising:
   obtaining, by a server in a service processing system, block data from an information storage blockchain node of a service consortium blockchain, wherein the service processing system comprises the server and the service consortium blockchain, wherein the service consortium blockchain is configured to receive and store the block data, wherein the service consortium blockchain is an insurance service consortium, wherein the information storage blockchain node is a blockchain node in the service consortium blockchain, and wherein obtaining the block data from the information storage blockchain node comprises
   periodically pulling the block data, through an active pull mode, from the information storage blockchain node of the service consortium blockchain, or
   monitoring, through a monitor pull mode, the block data in the information storage blockchain node and subsequently pulling the block data from the information storage blockchain node after monitoring the block data;
   storing, by the server, the block data from the information storage blockchain node of the service consortium blockchain in a local database, wherein the local database is local to the server;
   receiving, by the server, a service processing request from a user device, wherein the service processing request comprises an identity of a user of the user device and service information of the user, and wherein the service processing request is a case reporting request and comprises medical visit information of the user;
searching, by the server, the block data in the local database for service data related to the user based on the identity of the user and the service information of the user, comprising:
  searching the block data in the local database for plan details of the user and medical data of the user based on the identity of the user and the medical visit information of the user;
based on the service data related to the user, determining, by the server, service processing information to be used in a service processing operation performed responsive to the service processing request, comprising:
  determining case reporting information to be used in a case reporting based on the plan details of the user and the medical data of the user; and
completing, by the server, the service processing operation for the user based on the service processing information, comprising:
  completing the case reporting for the user based on the case reporting information.

2. The computer-implemented method of claim 1, further comprising:
after the receiving the service processing request, sending a service authorization request to the user device; and
searching for processing status of the user based on the identity of the user when a service authorization of the user is obtained from the user device.

3. The computer-implemented method of claim 2, further comprising:
sending a processing failure identifier to the user device when the processing status of the user is "being processed" or "processing completed".

4. The computer-implemented method of claim 2, further comprising:
searching for the service data related to the user based on the identity of the user and the service information of the user when the processing status of the user is empty.

5. The computer-implemented method of claim 1, wherein completing the service processing operation for the user based on the service processing information comprises:
calculating indemnity amounts corresponding to all items of the service information based on an indemnity limit and an indemnity proportion in the plan details, and adding them up to obtain a total to-be-indemnified amount;
comparing the total to-be-indemnified amount with a maximum indemnity limit of the plan details;
determining the total to-be-indemnified amount as a first indemnity amount of the user when the total to-be-indemnified amount is less than or equal to the maximum indemnity limit, or
determining the maximum indemnity limit as a second indemnity amount of the user when the total to-be-indemnified amount is greater than the maximum indemnity limit; and
completing the service processing operation for the user based on the first indemnity amount of the user when the total to-be-indemnified amount is less than or equal to the maximum indemnity limit, or based on the second indemnity amount of the user when the total to-be-indemnified amount is greater than the maximum indemnity limit.

6. The computer-implemented method of claim 1, wherein network nodes in the service consortium blockchain comprise a service-related agency node, a device node of a regulatory agency, and a service device of an Internet platform accessing the service consortium blockchain.

7. The computer-implemented method of claim 1, further comprising:
after completing the service processing operation for the user based on the service processing information, sending processing status to the information storage blockchain node of the service consortium blockchain.

8. A non-transitory, computer-readable medium storing one or more instructions executable by a computer system to perform operations, comprising:
obtaining, by a server in a service processing system, block data from an information storage blockchain node of a service consortium blockchain, wherein the service processing system comprises the server and the service consortium blockchain, wherein the service consortium blockchain is configured to receive and store the block data, wherein the service consortium blockchain is an insurance service consortium, wherein the information storage blockchain node is a blockchain node in the service consortium blockchain, and wherein obtaining the block data from the information storage blockchain node comprises
  periodically pulling the block data, through an active pull mode, from the information storage blockchain node of the service consortium blockchain, or
  monitoring, through a monitor pull mode, the block data in the information storage blockchain node and subsequently pulling the block data from the information storage blockchain node after monitoring the block data;
storing, by the server, the block data from the information storage blockchain node of the service consortium blockchain in a local database, wherein the local database is local to the server;
receiving, by the server, a service processing request from a user device, wherein the service processing request comprises an identity of a user of the user device and service information of the user, and wherein the service processing request is a case reporting request and comprises medical visit information of the user;
searching, by the server, the block data in the local database for service data related to the user based on the identity of the user and the service information of the user, comprising:
  searching the block data in the local database for plan details of the user and medical data of the user based on the identity of the user and the medical visit information of the user;
based on the service data related to the user, determining, by the server, service processing information to be used in a service processing operation performed responsive to the service processing request, comprising:
  determining case reporting information to be used in a case reporting based on the plan details of the user and the medical data of the user; and
completing, by the server, the service processing operation for the user based on the service processing information, comprising:
  completing the case reporting for the user based on the case reporting information.

9. The non-transitory, computer-readable medium of claim 8, wherein the operations further comprise:
after the receiving the service processing request, sending a service authorization request to the user device; and searching for processing status of the user based on the identity of the user when a service authorization of the user is obtained from the user device.

10. The non-transitory, computer-readable medium of claim 9, wherein the operations further comprise:
sending a processing failure identifier to the user device when the processing status of the user is "being processed" or "processing completed".

11. The non-transitory, computer-readable medium of claim 9, wherein the operations further comprise:
searching for the service data related to the user based on the identity of the user and the service information of the user when the processing status of the user is empty.

12. The non-transitory, computer-readable medium of claim 8, wherein determining the service processing information to be used in the service processing operation performed responsive to the service processing request comprises:
determining that the user of the user device satisfies a predetermined processing condition based on the service information, the plan details, and the service data related to the user; and
responsive to determining that the user satisfies the predetermined processing condition, obtaining, from the service information based on the plan details, qualitative attribute information corresponding to a qualitative attribute of plan detail responsibility information, wherein the qualitative attribute information is the service processing information to be used in the service processing operation.

13. The non-transitory, computer-readable medium of claim 8, wherein completing the service processing operation for the user based on the service processing information comprises:
calculating indemnity amounts corresponding to all items of the service information based on an indemnity limit and an indemnity proportion in the plan details, and adding them up to obtain a total to-be-indemnified amount;
comparing the total to-be-indemnified amount with a maximum indemnity limit of the plan details;
determining the total to-be-indemnified amount as a first indemnity amount of the user when the total to-be-indemnified amount is less than or equal to the maximum indemnity limit, or
determining the maximum indemnity limit as a second indemnity amount of the user when the total to-be-indemnified amount is greater than the maximum indemnity limit; and
completing the service processing operation for the user based on the first indemnity amount of the user when the total to-be-indemnified amount is less than or equal to the maximum indemnity limit, or based on the second indemnity amount of the user when the total to-be-indemnified amount is greater than the maximum indemnity limit.

14. The non-transitory, computer-readable medium of claim 8, wherein network nodes in the service consortium blockchain comprise a service-related agency node, a device node of a regulatory agency, and a service device of an Internet platform accessing the service consortium blockchain.

15. The non-transitory, computer-readable medium of claim 8, wherein the operations further comprise:
after completing the service processing operation for the user based on the service processing information, sending processing status to the information storage blockchain node of the service consortium blockchain.

16. A computer-implemented system, comprising:
one or more computers; and
one or more computer memory devices interoperably coupled with the one or more computers and having tangible, non-transitory, machine-readable media storing one or more instructions that, when executed by the one or more computers, perform operations comprising:
obtaining, by a server in a service processing system, block data from an information storage blockchain node of a service consortium blockchain, wherein the service processing system comprises the server and the service consortium blockchain, wherein the service consortium blockchain is configured to receive and store the block data, wherein the service consortium blockchain is an insurance service consortium, wherein the information storage blockchain node is a blockchain node in the service consortium blockchain, and wherein obtaining the block data from the information storage blockchain node comprises
periodically pulling the block data, through an active pull mode, from the information storage blockchain node of the service consortium blockchain, or
monitoring, through a monitor pull mode, the block data in the information storage blockchain node and subsequently pulling the block data from the information storage blockchain node after monitoring the block data;
storing, by the server, the block data from the information storage blockchain node of the service consortium blockchain in a local database, wherein the local database is local to the server;
receiving, by the server, a service processing request from a user device, wherein the service processing request comprises an identity of a user of the user device and service information of the user, and wherein the service processing request is a case reporting request and comprises medical visit information of the user;
searching, by the server, the block data in the local database for service data related to the user based on the identity of the user and the service information of the users comprising:
searching the block data in the local database for plan details of the user and medical data of the user based on the identity of the user and the medical visit information of the user;
based on the service data related to the user, determining, by the server, service processing information to be used in a service processing operation performed responsive to the service processing request, comprising:
determining case reporting information to be used in a case reporting based on the plan details of the user and the medical data of the user; and
completing, by the server, the service processing operation for the user based on the service processing information, comprising:
completing the case reporting for the user based on the case reporting information.

17. The computer-implemented system of claim 16, wherein the operations further comprise:
after the receiving the service processing request, sending a service authorization request to the user device; and searching for processing status of the user based on the identity of the user when a service authorization of the user is obtained from the user device.

18. The computer-implemented system of claim 17, wherein the operations further comprise:
sending a processing failure identifier to the user device when the processing status of the user is "being processed" or "processing completed".

19. The computer-implemented system of claim 17, wherein the operations further comprise:
searching for the service data related to the user based on the identity of the user and the service information of the user when the processing status of the user is empty.

20. The computer-implemented system of claim 16, wherein determining the service processing information to be used in the service processing operation performed responsive to the service processing request comprises:
determining that the user of the user device satisfies a predetermined processing condition based on the service information, the plan details, and the service data related to the user; and
responsive to determining that the user satisfies the predetermined processing condition, obtaining, from the service information based on the plan details, qualitative attribute information corresponding to a qualitative attribute of plan detail responsibility information, wherein the qualitative attribute information is the service processing information to be used in the service processing operation.

21. The computer-implemented system of claim 16, wherein completing the service processing operation for the user based on the service processing information comprises:
calculating indemnity amounts corresponding to all items of the service information based on an indemnity limit and an indemnity proportion in the plan details, and adding them up to obtain a total to-be-indemnified amount;
comparing the total to-be-indemnified amount with a maximum indemnity limit of the plan details;
determining the total to-be-indemnified amount as a first indemnity amount of the user when the total to-be-indemnified amount is less than or equal to the maximum indemnity limit, or
determining the maximum indemnity limit as a second indemnity amount of the user when the total to-be-indemnified amount is greater than the maximum indemnity limit; and
completing the service processing operation for the user based on the first indemnity amount of the user when the total to-be-indemnified amount is less than or equal to the maximum indemnity limit, or based on the second indemnity amount of the user when the total to-be-indemnified amount is greater than the maximum indemnity limit.

22. The computer-implemented system of claim 16, wherein network nodes in the service consortium blockchain comprise a service-related agency node, a device node of a regulatory agency, and a service device of an Internet platform accessing the service consortium blockchain.

23. The computer-implemented system of claim 16, wherein the operations further comprise:
after completing the service processing operation for the user based on the service processing information, sending processing status to the information storage blockchain node of the service consortium blockchain.

24. The computer-implemented method of claim 1, wherein determining, by the server, the service processing information to be used in the service processing operation performed responsive to the service processing request comprises:
determining that the user of the user device satisfies a predetermined processing condition based on the service information, the plan details, and the service data related to the user; and
responsive to determining that the user satisfies the predetermined processing condition, obtaining, from the service information based on the plan details, qualitative attribute information corresponding to a qualitative attribute of plan detail responsibility information, wherein the qualitative attribute information is the service processing information to be used in the service processing operation.

25. The computer-implemented method of claim 1, wherein the block data is obtained from the information storage blockchain node based on a block height of data added to the information storage blockchain node since the information storage blockchain node was last accessed by the server.

26. The non-transitory, computer-readable medium of claim 8, wherein the block data is obtained from the information storage blockchain node based on a block height of data added to the information storage blockchain node since the information storage blockchain node was last accessed by the server.

27. The computer-implemented system of claim 16, wherein the block data is obtained from the information storage blockchain node based on a block height of data added to the information storage blockchain node since the information storage blockchain node was last accessed by the server.

* * * * *